United States Patent
Bailey et al.

(10) Patent No.: US 8,733,352 B2
(45) Date of Patent: May 27, 2014

(54) PULSE OXYGEN SYSTEM

(75) Inventors: Delbert B. Bailey, Bellevue, WA (US); Karen C. Bradshaw, Lynnwood, WA (US); Paul Kinzer, Bothell, WA (US)

(73) Assignee: The Boeing Company, Chicago, IL (US)

( * ) Notice: Subject to any disclaimer, the term of this patent is extended or adjusted under 35 U.S.C. 154(b) by 333 days.

(21) Appl. No.: 13/251,169

(22) Filed: Sep. 30, 2011

(65) Prior Publication Data

US 2013/0081627 A1    Apr. 4, 2013

(51) Int. Cl.
*A61M 16/00* (2006.01)
*A62B 7/04* (2006.01)
*F16K 31/26* (2006.01)
*A62B 7/00* (2006.01)
*A62B 9/02* (2006.01)

(52) U.S. Cl.
USPC ............. 128/204.29; 128/204.21; 128/205.24

(58) Field of Classification Search
CPC ........ A62B 7/14; A62B 25/005; B64D 13/00; B64D 13/02; B64D 13/04; B64D 13/06; B64D 11/00
USPC ............. 128/204.18, 204.21, 204.22, 204.26, 128/204.29, 205.24
See application file for complete search history.

(56) References Cited

U.S. PATENT DOCUMENTS

| 6,220,244 B1 | 4/2001 | McLaughlin | |
| 2006/0266357 A1* | 11/2006 | McCombs et al. | 128/204.26 |
| 2008/0000480 A1* | 1/2008 | Cannon | 128/205.25 |
| 2010/0139658 A1* | 6/2010 | Wenzel et al. | 128/204.22 |

FOREIGN PATENT DOCUMENTS

| WO | 2008/138930 A2 | 11/2008 |
| WO | WO2008/138930 | * 11/2008 |
| WO | 2011/033525 A2 | 3/2011 |
| WO | WO2011/033525 | * 3/2011 |

OTHER PUBLICATIONS

International Search Report and the Written Opinion of the International Searching Authority mailed on Sep. 5, 2013 for PCT Application No. PCT/US2012/053112 filed on Aug. 30, 2012—International Searching Authority—European Patent Office.

* cited by examiner

*Primary Examiner* — Kristen Matter
(74) *Attorney, Agent, or Firm* — Ameh IP; Elane Toosi; Lowell Campbell (57) ABSTRACT

A pulse oxygen system and methods for providing oxygen to a user are disclosed. An oxygen mask coupled to a metering valve is provided to a user. An oxygen prescription delivery amount is determined based on and as a function of a real-time operation condition. A metering valve timing is calculated based on the oxygen prescription delivery amount to obtain a pulse delivery time. A pressure and time regulated flow of the oxygen prescription delivery amount of pulsed oxygen is then dispensed to the oxygen mask for a duration of the pulse delivery time in response to detecting the user breathing through the oxygen mask.

20 Claims, 7 Drawing Sheets

PULSE OXYGEN SYSTEM

FIELD

Embodiments of the present disclosure relate generally to non-chemical oxygen systems. More particularly, embodiments of the present disclosure relate to non-chemical pulse oxygen systems.

BACKGROUND

Government regulations require oxygen to be installed on many aircraft to protect passengers from low oxygen conditions in an event of an aircraft decompression. Chemical oxygen systems have been used for about 30 years to provide low oxygen protection on commercial jet transport aircraft. Chemicals inside a container are required to provide a reaction necessary to produce a byproduct of nearly pure oxygen. Passengers can tamper with the chemical oxygen systems to use the heat that it produces during the reaction and the chemicals themselves for things other than their original purpose. Chemical oxygen systems may be a non-optimal security condition when installed in certain locations on a commercial aircraft, thus changes have been mandated to remove chemical oxygen systems from the aircraft.

SUMMARY

A pulse oxygen system and methods for providing oxygen to a user are disclosed. An oxygen mask coupled to a metering valve is provided to a user. An oxygen prescription delivery amount is determined based on and as a function of a real-time operational condition. A metering valve timing is calculated based on the oxygen prescription delivery amount to obtain a pulse delivery time. A pressure and time regulated flow of the oxygen prescription delivery amount of pulsed oxygen is then dispensed to the oxygen mask for a duration of the pulse delivery time in response to detecting the user breathing through the oxygen mask.

The pulse oxygen system is generally lighter, smaller, and safer than existing systems. The pulse oxygen system produces a required oxygen quantity to passengers to protect them from low oxygen conditions in an event of an aircraft decompression without the use of chemicals or heat that are typical of chemical oxygen systems. Thereby, the pulse oxygen system removes potential issues of flammable chemicals and heat generation during activation, providing for a substantially optimal system. Further, packaging of the pulse oxygen system can be of a similar size as a chemical oxygen system, so the pulse oxygen system can be a direct replacement for the chemical oxygen system when installed in an aircraft. The pulse oxygen system can also provide more oxygen for longer periods of low oxygen conditions protection than chemical oxygen systems giving the pulse oxygen system advantages for many low oxygen conditions.

In an embodiment, a method for providing pulsed supplemental oxygen to a user provides an oxygen mask coupled to a metering valve to a user. The method then determines an oxygen prescription delivery amount based on and as a function of real-time operation condition. The method further calculates a metering valve timing based on the oxygen prescription delivery amount to obtain a pulse delivery time. The method then dispenses a pressure and time regulated flow of the oxygen prescription delivery amount of pulsed oxygen to the oxygen mask for a duration of the pulse delivery time in response to detecting the user breathing through the oxygen mask.

In another embodiment, a pulse oxygen system comprises an oxygen mask, a metering valve timing calculation module, and a metering valve. The oxygen mask provides a flow of pulsed oxygen to a user. The metering valve timing calculation module calculates a metering valve timing to provide a pulse delivery time based on the oxygen prescription delivery amount corresponding to a real-time operation condition. The metering valve provides the flow of pulsed oxygen in response to detecting the user breathing through the oxygen mask and dispenses a pressure and time regulated flow of the oxygen prescription delivery amount of the pulsed oxygen to the oxygen mask for a duration of the pulse delivery time.

In yet another embodiment, a method of providing a pulse oxygen system in a portable pulse oxygen package provides an oxygen mask operable to provide a flow of pulsed oxygen to a user. The method further provides a metering valve timing calculation module operable to calculate a metering valve timing based on an oxygen prescription delivery amount to obtain a pulse delivery time. The method then provides a metering valve coupled to the oxygen mask and operable to provide the flow of pulsed oxygen in response to detecting the user breathing through the oxygen mask and dispense a pressure and time regulated flow of the oxygen prescription delivery amount of the pulsed oxygen to the oxygen mask for a duration of the pulse delivery time.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF DRAWINGS

A more complete understanding of embodiments of the present disclosure may be derived by referring to the detailed description and claims when considered in conjunction with the following figures, wherein like reference numbers refer to similar elements throughout the figures. The figures are provided to facilitate understanding of the disclosure without limiting the breadth, scope, scale, or applicability of the disclosure. The drawings are not necessarily made to scale.

DETAILED DESCRIPTION

The following detailed description is exemplary in nature and is not intended to limit the disclosure or the application and uses of the embodiments of the disclosure. Descriptions of specific devices, techniques, and applications are provided only as examples. Modifications to the examples described herein will be readily apparent to those of ordinary skill in the art, and the general principles defined herein may be applied to other examples and applications without departing from the spirit and scope of the disclosure. Furthermore, there is no intention to be bound by any expressed or implied theory presented in the preceding field, background, summary or the following detailed description. The present disclosure should be accorded scope consistent with the claims, and not limited to the examples described and shown herein.

Embodiments of the disclosure may be described herein in terms of functional and/or logical block components and various processing steps. It should be appreciated that such block components may be realized by any number of hardware, software, and/or firmware components configured to perform the specified functions. For the sake of brevity, conventional techniques and components related to oxygen generators, fluid dynamics, systems packaging, manufacturing, sensors, and other functional aspects of the systems (and the individual operating components of the systems) may not be described in detail herein. In addition, those skilled in the art will appreciate that embodiments of the present disclosure may be practiced in conjunction with a variety of structural bodies, and that the embodiments described herein are merely example embodiments of the disclosure.

Embodiments of the disclosure are described herein in the context of a practical non-limiting application, namely, a pulse oxygen system for an aircraft. Embodiments of the disclosure, however, are not limited to such aircraft applications, and the techniques described herein may also be utilized in other fluid dynamic applications. For example, embodiments may be applicable to trains, buses, spacecraft, vehicles, submarines, buildings, outdoor activity applications such as; high altitude mountain hiking, and ocean diving, and the like.

As would be apparent to one of ordinary skill in the art after reading this description, the following are examples and embodiments of the disclosure and are not limited to operating in accordance with these examples. Other embodiments may be utilized and structural changes may be made without departing from the scope of the exemplary embodiments of the present disclosure.

Some systems use chemical oxygen generators. As mentioned above, chemical oxygen generators can be a non-optimal security condition when installed in certain locations on a commercial aircraft, and changes have been mandated to remove this non-optimal condition from aircraft.

Embodiments of the disclosure provide required oxygen to passengers without chemicals and without producing heat using a pulse oxygen system. Thereby, issues of flammable chemicals and heat generation during activation are removed. Packaging of the pulse oxygen system can be of a similar size as a chemical oxygen system, so the pulse oxygen system can be a direct replacement for the chemical oxygen system when installed in an aircraft. Embodiments of the pulse oxygen system can also provide more oxygen for longer periods of low oxygen conditions protection than chemical oxygen systems giving it advantages for many flight profiles.

Figure 1:
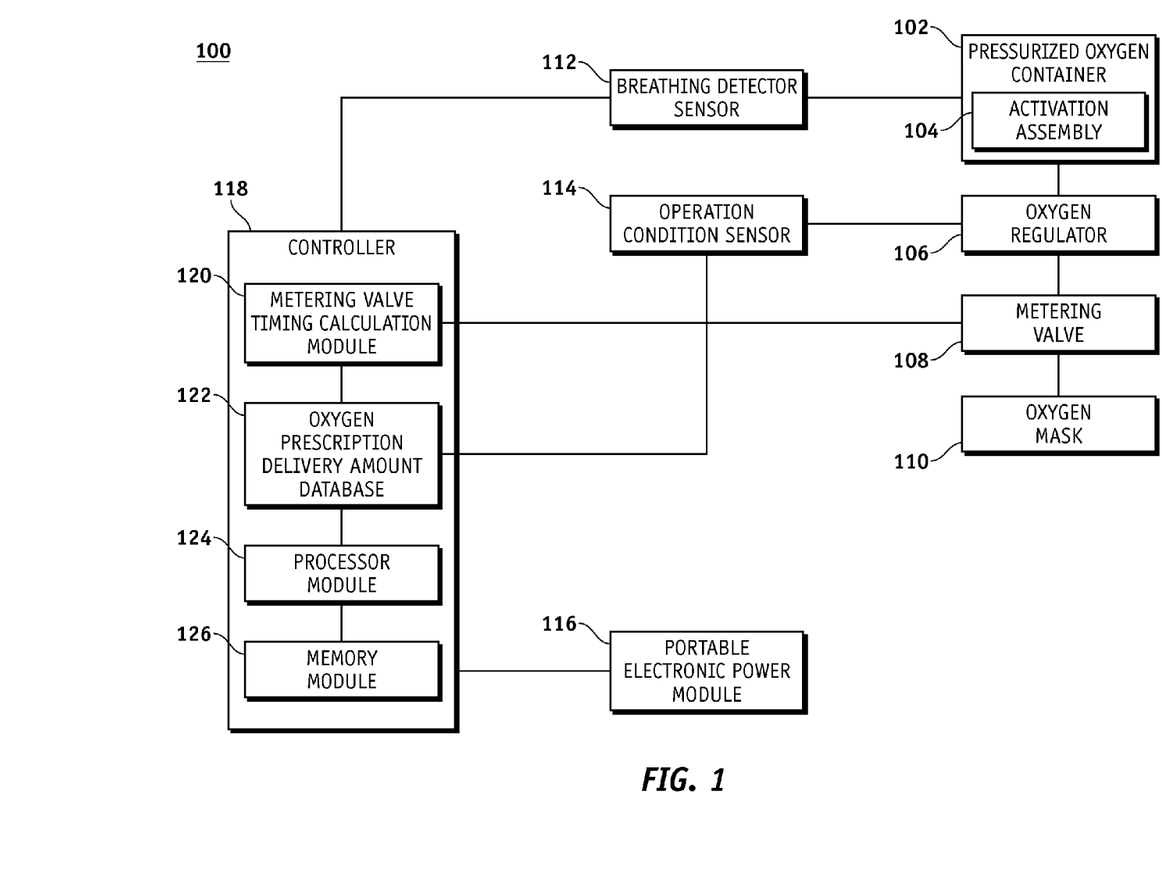
FIG. 1 is an illustration of an exemplary functional block diagram of a pulse oxygen system according to an embodiment of the disclosure.

FIG. 1 is an illustration of an exemplary functional block diagram of a pulse oxygen system (system 100) according to an embodiment of the disclosure. The system 100 may comprise a pressurized oxygen container 102, an oxygen regulator 106, a metering valve 108, at least one oxygen mask 110, a breathing detector sensor 112, an operation condition sensor 114, a portable electronic power module 116, and a controller 118.

A practical system 100 may comprise any number of input modules, any number of processor modules, any number of memory modules, any number of sensors, any number of battery modules, and any number of other modules. The illustrated system 100 depicts a simple embodiment for ease of description. These and other elements of the system 100 are interconnected together, allowing communication between the various elements of the system 100. Those of skill in the art will understand that the various illustrative blocks, modules, circuits, and processing logic described in connection with the embodiments disclosed herein may be implemented in hardware, computer-readable software, firmware, or any practical combination thereof.

To illustrate clearly this interchangeability and compatibility of hardware, firmware, and software, various illustrative components, blocks, modules, circuits, and steps are described generally in terms of their functionality. Whether such functionality is implemented as hardware, firmware, or software depends upon the particular application and design constraints imposed on the overall system. Those familiar with the concepts described herein may implement such functionality in a suitable manner for each particular application, but such implementation decisions should not be interpreted as causing a departure from the scope of the present disclosure.

The pressurized oxygen container 102 is coupled to the oxygen regulator 106 and the breathing detector sensor 112. The pressurized oxygen container 102 comprises an assembly valve 104 that is activated in response to a user breathing through the oxygen mask 110. When a user takes a breath through the oxygen mask 110, the assembly valve 104 receives an activation signal from the breathing detector sensor 112 indicating the user is taking a breath. The assembly valve 104 is then opened to initiate a flow of an oxygen prescription delivery amount of pulsed oxygen in response to receiving the activation signal thus detecting the user breathing through the oxygen mask 110. The pressurized oxygen container 102 comprises pressurized oxygen at a pressure of about 3000 psi, 4500 psi, or other similar pressure.

The oxygen regulator 106 is coupled the pressurized oxygen container 102, and the metering valve 108. The oxygen regulator 106 receives oxygen from the pressurized oxygen container 102 at a high pressure (e.g., 5000 psi) and reduces the received pressure to an amount suitable for use by the metering valve 108 (e.g. 50 psi).

The metering valve 108 is coupled to the oxygen regulator 106, and the oxygen mask 110. The metering valve 108 is operable to provide the flow of pulsed oxygen in response to detecting the user breathing and dispense a pressure and time regulated flow of the oxygen prescription delivery amount of the pulsed oxygen to the user for a duration of a pulse delivery time through the oxygen mask 110. Providing a flow of pulsed oxygen, instead of a continuous flow of the oxygen provided by the existing systems to the user, provides more oxygen for longer periods of low oxygen conditions protection than chemical oxygen systems giving the pulse oxygen system described herein advantages for many low oxygen conditions.

The oxygen mask 110 is coupled to the metering valve 108 and is operable to provide a flow of pulsed oxygen to the user though a mask hose (not shown) dispensed by the metering valve 108.

The breathing detector sensor 112 is coupled to the oxygen mask 110 and is operable to initiate the flow of the oxygen prescription delivery amount of the pulsed oxygen in response to detecting the user breathing through the oxygen mask 110. As mentioned above, when the user takes a breath through the oxygen mask 110, the assembly valve 104 receives an activation signal from the breathing detector sensor 112 through the controller 118 indicating the user is taking a breath. The assembly valve 104 is then opened to initiate a flow of an oxygen prescription delivery amount of pulsed oxygen in response to receiving the activation signal.

The operation condition sensor 114 is coupled to the controller 118 and is operable to detect the real-time operation condition. The real-time operation condition, may comprise, for example but without limitation, pressure in a decompressed aircraft cabin, pressure in a decompressed high speed train, pressure in high altitudes mountains, pressure in a high smoke environments, amount of temperature, or other operation condition.

The portable electronic power module 116 is operable to power the pulse oxygen system 100. The portable electronic power module 116 may comprise, for example but without limitation, a battery, a cell stack, and other portable electronic device.

The controller 118 is operable in part to calculate the metering valve timing based on the oxygen prescription delivery amount to obtain a pulse delivery time. The controller comprises a metering valve timing calculation module 120, an oxygen prescription delivery amount database 122, a processor module 124, and a memory module 126.

The metering valve timing calculation module 120 is operable to calculate a metering valve timing based on the oxygen prescription delivery amount to obtain the pulse delivery time. The operation condition sensor 114 detects the operation condition, and sends the real-time operation condition to the controller 118. The controller 118 then determines the oxygen prescription delivery amount by accessing the oxygen prescription delivery amount database 122. In this manner, the controller 118 enters the real-time operation condition to the oxygen prescription delivery amount database 122 and searches for the oxygen prescription delivery amount corresponding to the real-time operation condition.

For example but without limitation, a user may need about 85 ml to about 100 ml of oxygen delivery per breath at the real-time operation condition at a pressure range of about 5.0 psi to about 6.0 psi, or other suitable flow rate. The metering valve timing calculation module 120 then determines the metering valve timing necessary to keep the metering valve 108 open for providing the oxygen prescription delivery amount of the pulsed oxygen to the user. The metering valve timing may be about ⅓rd of a second, about ¼th of a second, and the like, depending on the real-time operation condition.

The oxygen prescription delivery amount database 122 comprises pre-determined experimental data for determining the oxygen prescription delivery amount based on and as a function of the real-time operation condition. For example, the oxygen prescription delivery amount database 122 may comprise the oxygen prescription delivery amount to passengers in case of decompression on an aircraft corresponding to various altitudes.

The processor module 124 comprises processing logic that is configured to carry out the functions, techniques, and processing tasks associated with the operation of the system 100. In particular, the processing logic is configured to support the system 100 described herein. For example, the processor module 124 may direct the metering valve timing calculation module 120 to calculate a pulse delivery time for pulsing the flow of oxygen to the user.

For another example, the processor module 124 may provide the real-time operation condition from the operation condition sensor 114 to the oxygen prescription delivery amount database 122. In this manner, the processor module 124 determines the oxygen prescription delivery amount based on the real-time operation condition by accessing the oxygen prescription delivery amount database 122 and determining the oxygen prescription delivery amount corresponding to the operation condition.

The processor module 124 may be implemented, or realized, with a general purpose processor, a content addressable memory, a digital signal processor, an application specific integrated circuit, a field programmable gate array, any suitable programmable logic device, discrete gate or transistor logic, discrete hardware components, or any combination thereof, designed to perform the functions described herein. In this manner, a processor may be realized as a microprocessor, a controller, a microcontroller, a state machine, or the like. A processor may also be implemented as a combination of computing devices, e.g., a combination of a digital signal processor and a microprocessor, a plurality of microprocessors, one or more microprocessors in conjunction with a digital signal processor core, or any other such configuration.

The memory module 126 may comprise a data storage area with memory formatted to support the operation of the system 100. The memory module 126 is configured to store, maintain, and provide data as needed to support the functionality of the system 100. For example, the memory module 126 may store the real-time operation condition, and other data, in the oxygen prescription delivery amount database 122. In practical embodiments, the memory module 126 may comprise, for example but without limitation, a non-volatile storage device (non-volatile semiconductor memory, hard disk device, optical disk device, and the like), a random access storage device (for example, SRAM, DRAM), or any other form of storage medium known in the art.

The memory module 126 may be coupled to the processor module 124 and configured to store, for example but without limitation, an operation condition database, the oxygen prescription delivery amount database 122, a computer program that is executed by the processor module 124, an operating system, an application program, tentative data used in executing a program, and the like. Additionally, the memory module 604 may represent a dynamically updating database containing a table for updating the database, and the like.

The memory module 126 may be coupled to the processor module 124 such that the processor module 124 can read information from and write information to the memory module 126. For example, the processor module 124 may access the memory module 126 to access real-time operation condition, the oxygen prescription delivery amount, or other data.

As an example, the processor module 124 and memory module 126 may reside in respective application specific integrated circuits (ASICs). The memory module 126 may also be integrated into the processor module 124. In an embodiment, the memory module 126 may comprise a cache memory for storing temporary variables or other intermediate information during execution of instructions to be executed by the processor module 124.

Figure 2:
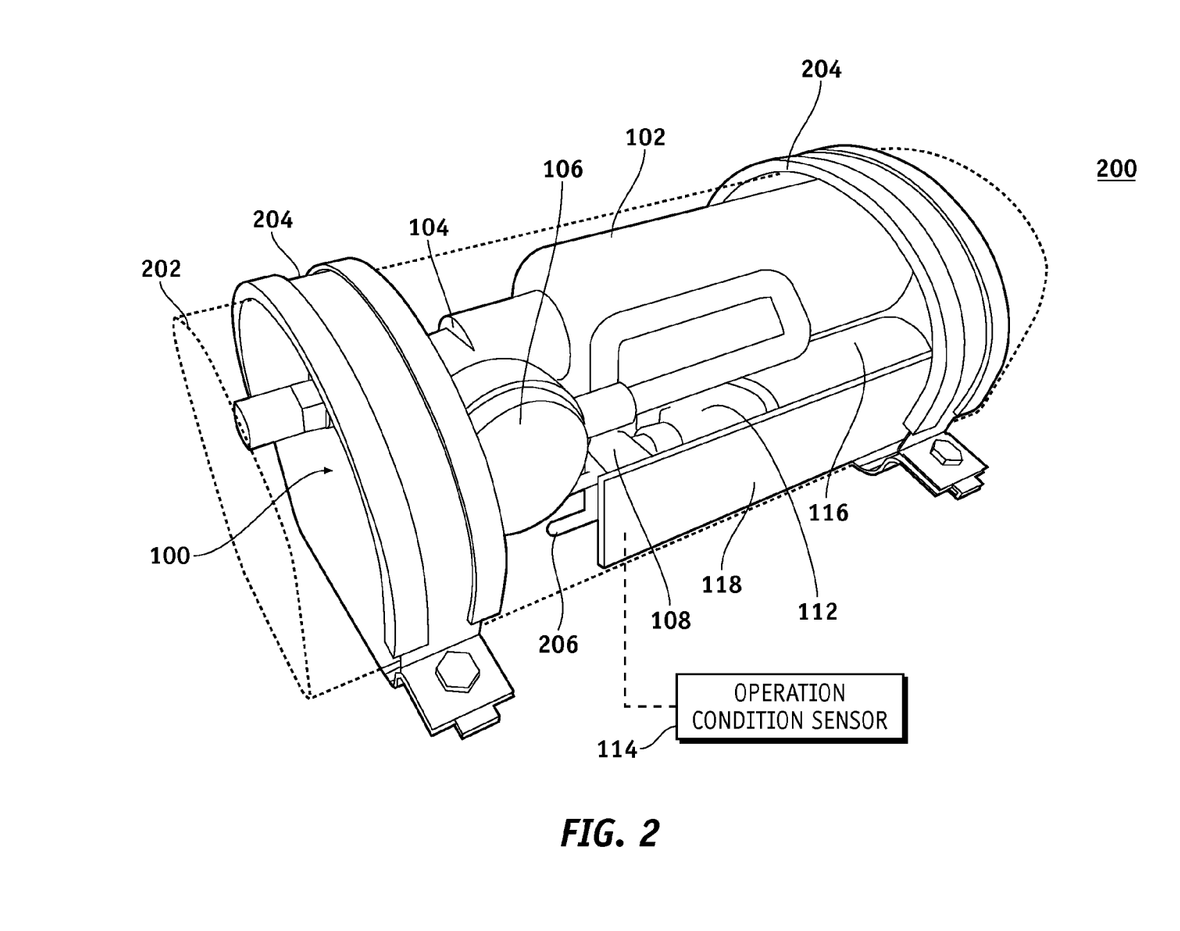
FIG. 2 is an illustration of an exemplary portable pulse oxygen package according to an embodiment of the disclosure.

FIG. 2 is an illustration of an exemplary portable pulsed oxygen package 200 (package 200) showing the system 100 (FIG. 1) packaged in a canister 202 according to an embodiment of the disclosure. The portable pulse oxygen package 200 may have functions, material, and structures that are similar to the embodiments shown in FIG. 1. Therefore, common features, functions, and elements may not be redundantly described here. In one embodiment, the portable pulse oxygen system 100 is packaged in the canister 202 and secured by brackets 204. An oxygen mask tubing can be coupled to a mask hose connector 206 to deliver pulsed oxygen to the user.

As mentioned above, packaging of the pulse oxygen system 100 can be of a similar size as the chemical oxygen system so the package 200 can be a direct replacement for the chemical oxygen system when installed in an aircraft. Various means of installing the package 200 comprising the pulse oxygen system 100 are shown in FIGS. 6-9.

Figure 3:
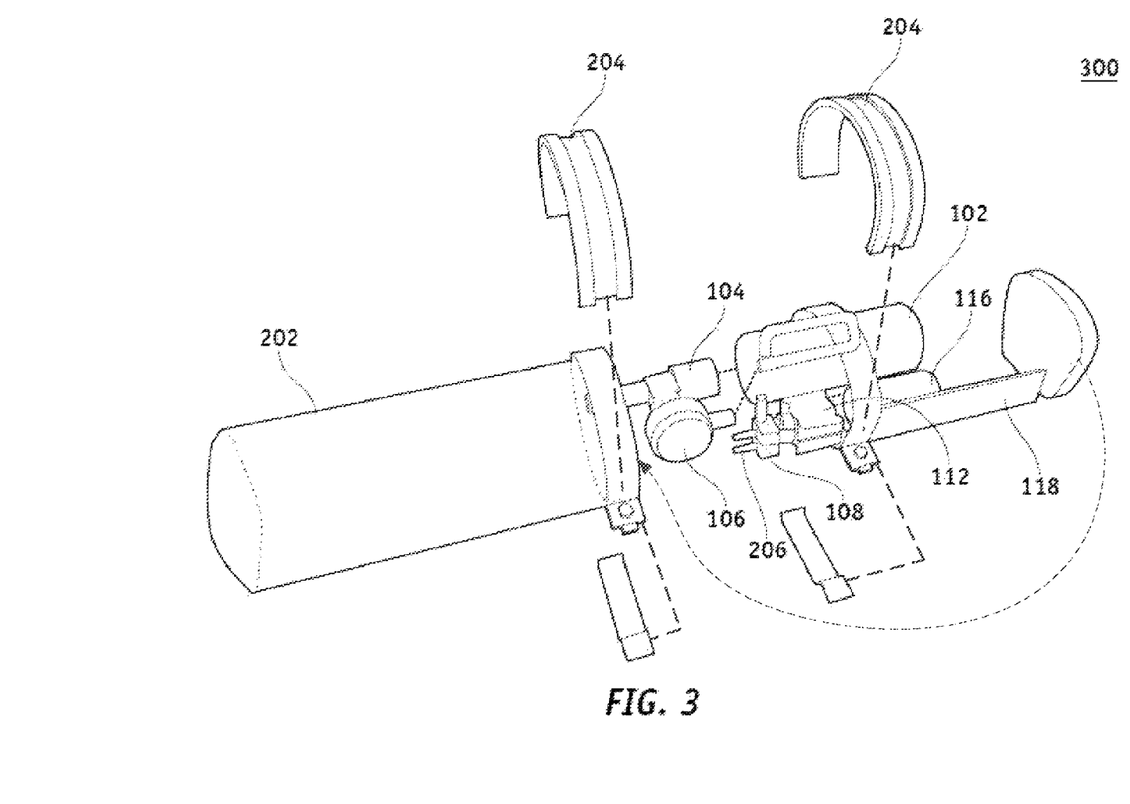
FIG. 3 is an illustration of the pulse oxygen package of FIG. 2 showing disassembled components thereof.

FIG. 3 is an illustration of the package 200 comprising the pulse oxygen system 100 showing disassembled components 300 thereof.

Figure 4:
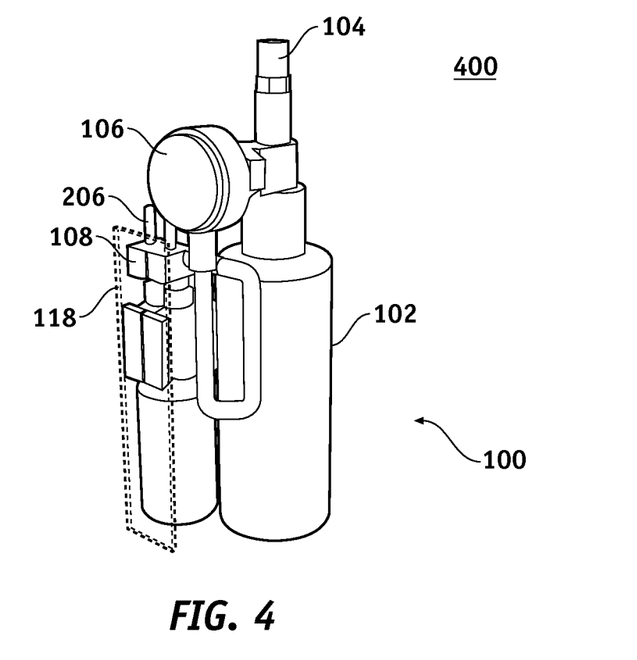
FIG. 4 is an illustration of a perspective view of a pulse oxygen system according to an embodiment of the disclosure.

FIG. 4 is an illustration of a perspective view 400 of the pulse oxygen system 100 of FIGS. 1-2 according to an embodiment of the disclosure.

Figure 5:
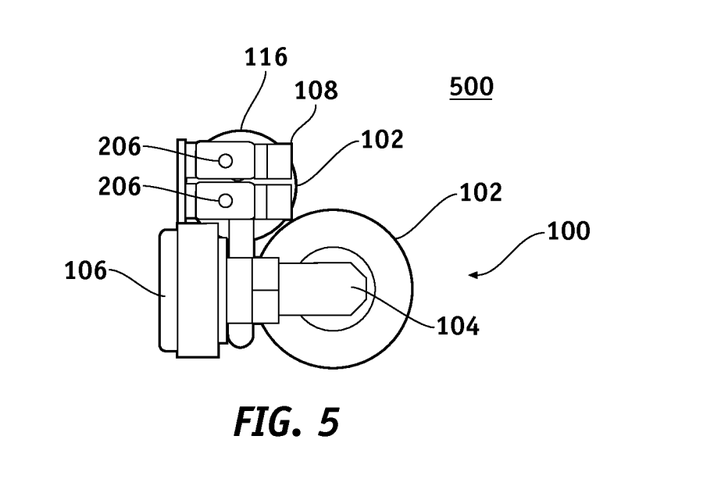
FIG. 5 is an illustration of a top view of a pulse oxygen system according to an embodiment of the disclosure.
Figures 6, 8:
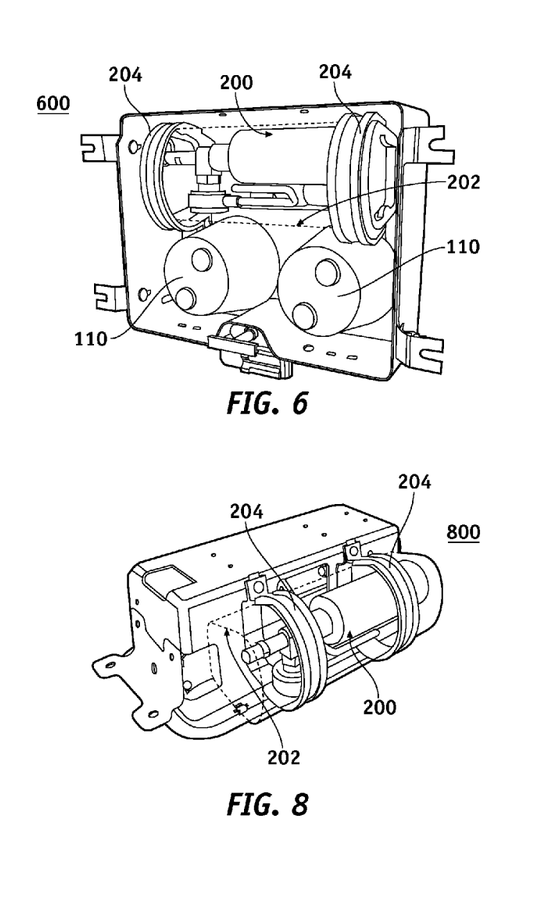
FIGS. 6-9 are illustrations of an exemplary pulse oxygen package showing various installation configurations according to various embodiment of the disclosure.
Figure 7:
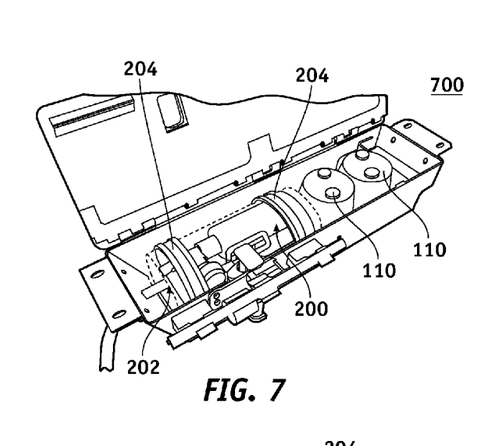
Figure 9:
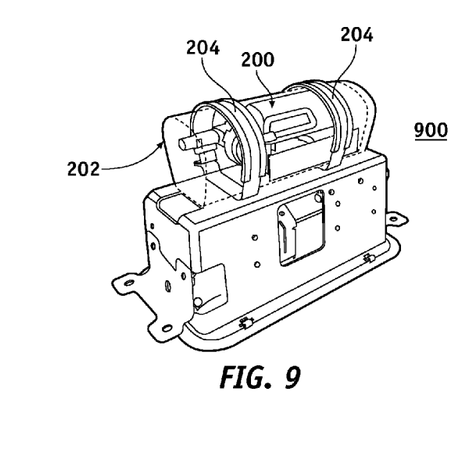

FIG. 5 is an illustration of a top view 500 of the pulse oxygen system 100 of FIGS. 1-2 according to an embodiment of the disclosure.

FIGS. 6-9 are illustrations of various installation configurations 600, 700, 800, and 900 of the package 200 according to various embodiment of the disclosure. Embodiments shown in FIGS. 6-9 may have functions, material, and structures that are similar to the embodiments shown in FIGS. 1-5. Therefore, common features, functions, and elements may not be redundantly described here. FIGS. 6-9 are described below in connection with FIGS. 1-2.

As mentioned above the pulsed oxygen system 100 (FIG. 1) is packaged in the container 202 (FIG. 2) and enclosed by the brackets 204 (FIG. 2) to form the package 200. Each of the installation configurations 600, 700, 800, and 900 may comprise the package 200, and at least one oxygen mask 110. Each oxygen mask 110 is coupled to the pulse oxygen system 100 (FIG. 1) via the mask hose (not shown) though the mask hose connector 206 (FIG. 2). Each oxygen mask 110 is operable to independently communicate with the metering valve 108 such that a flow of pulsed oxygen dispensed by the metering valve 108 is provided to the user of respective oxygen mask 110.

Figure 10:
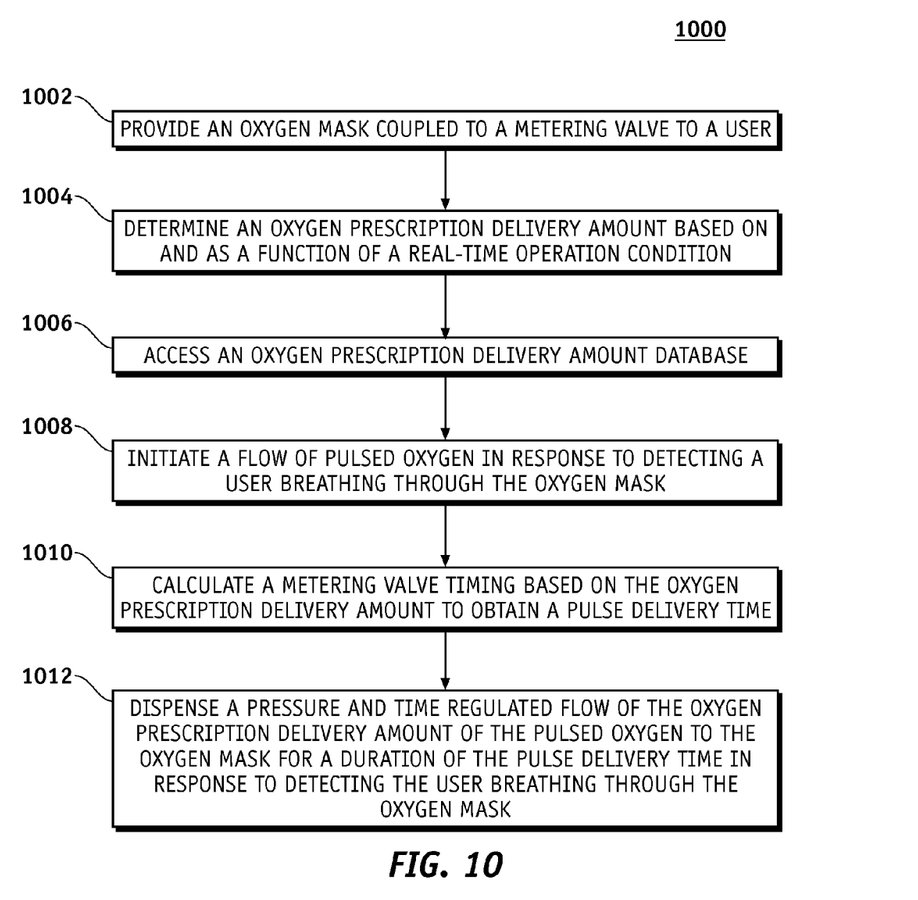
FIG. 10 is an illustration of an exemplary flowchart showing a process for providing pulsed supplemental oxygen to a user according to an embodiment of the disclosure.

FIG. 10 is an illustration of an exemplary flowchart showing a process 1000 for providing pulsed supplemental oxygen to a user according to an embodiment of the disclosure. The various tasks performed in connection with the process 1000 may be performed mechanically, by software, hardware, firmware, a computer-readable medium having computer executable instructions for performing the processes methods, or any combination thereof. For illustrative purposes, the following description of the process 1000 may refer to elements mentioned above in connection with FIGS. 1-9.

In practical embodiments, portions of the process 1000 may be performed by the oxygen container 102, the oxygen regulator 106, the metering valve 108, the oxygen mask 110, the breathing detector sensor 112, the operation condition sensor 114, the portable electronic power module 116, and the controller 118 etc. Process 1000 may have functions, material, and structures that are similar to the embodiments shown in FIGS. 1-9. Therefore, common features, functions, and elements may not be redundantly described here.

Process 1000 may begin by providing an oxygen mask such as the oxygen mask 110 coupled to a metering valve such as the metering valve 108 to the user (task 1002).

Process 1000 may continue by determining an oxygen prescription delivery amount based on and as a function of the real-time operation condition (task 1004).

Process 1000 determines the oxygen prescription delivery amount by the controller 118 accessing the oxygen prescription delivery amount database 122 (task 1006) as explained above. As mentioned above, the real-time operation condition comprises, for example but without limitation, a pressure in a decompressed aircraft cabin, a pressure in a decompressed high speed train, a pressure in high altitudes mountains, an amount of temperature, or other condition. The user may comprise, for example but without limited, a passenger onboard a decompressed aircraft cabin, a mountain hiker, a glider, an astronaut, a diver, or other user.

Process 1000 may continue by initiating the flow of the pulsed oxygen in response to detecting the user breathing through the oxygen mask 110 (task 1008).

Process 1000 may continue by calculating a metering valve timing based on the oxygen prescription delivery amount to obtain a pulse delivery time (task 1010).

Process 1000 may continue by dispensing a pressure and time regulated flow of the oxygen prescription delivery amount of the pulsed oxygen to the oxygen mask 110 for a duration of the pulse delivery time in response to a breathing detector sensor such as the breathing detector sensor 112 detecting the user breathing through the oxygen mask 110 (task 1012).

Figure 11:
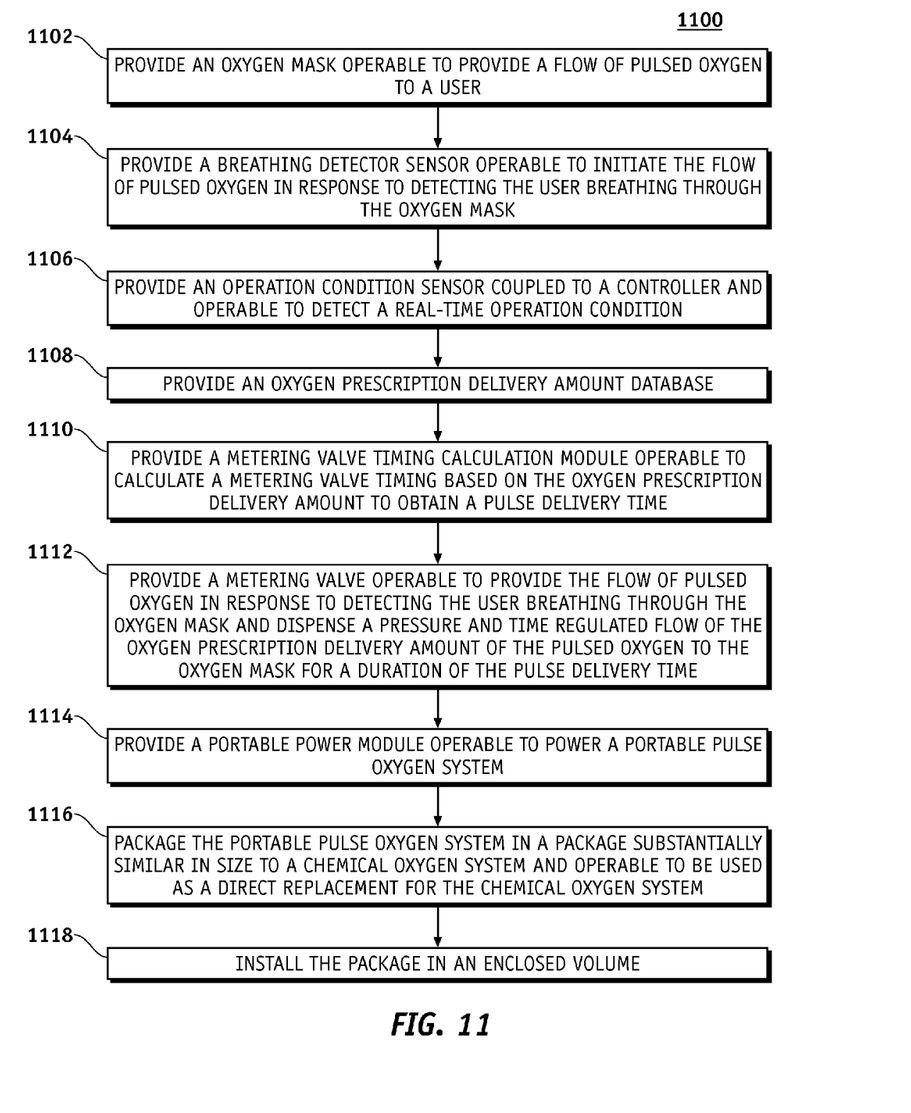
FIG. 11 is an illustration of an exemplary flowchart showing a process for providing a portable pulse oxygen package according to an embodiment of the disclosure.

FIG. 11 is an illustration of an exemplary flowchart showing a process 1100 for providing the portable pulse oxygen system 100 in a portable pulse oxygen package 200 according to an embodiment of the disclosure. The various tasks performed in connection with the process 1100 may be performed mechanically, by software, hardware, firmware, or any combination thereof. For illustrative purposes, the following description of the process 1100 may refer to elements mentioned above in connection with FIGS. 1-9.

In practical embodiments, portions of the process 1100 may be performed by the oxygen container 102, the oxygen regulator 106, the metering valve 108, the oxygen mask 110, the breathing detector sensor 112, the real-time operation condition sensor 114, the portable electronic power module 116, and the controller 118, the package 200, etc. Process 1100 may have functions, material, and structures that are similar to the embodiments shown in FIGS. 1-6. Therefore, common features, functions, and elements may not be redundantly described here.

Process 1100 may begin by providing an oxygen mask such as the oxygen mask 110 operable to provide a flow of pulsed oxygen to the user (task 1102).

Process 1100 may continue by providing a breathing detector sensor such as the breathing detector sensor 112 operable to initiate the flow of the pulsed oxygen in response to detecting the user breathing through the oxygen mask 110 (task 1104).

Process 1100 may continue by providing a real-time operation condition sensor such as the operation condition sensor 114 coupled a controller such as the controller 118 and operable to detect the real-time operation condition (1106).

Process 1100 may continue by providing an oxygen prescription delivery amount database such as the oxygen prescription delivery amount database 122 (1108). The oxygen prescription delivery amount database 122 comprises data base fields for oxygen prescription delivery amounts corresponding to various operation conditions.

Process 1100 may continue by providing a metering valve timing calculation module such as the metering valve timing calculation module 120 operable to calculate a metering valve timing based on the oxygen prescription delivery amount to obtain a pulse delivery time (task 1110).

Process 1100 may continue by providing a metering valve such as the metering valve 108 operable to provide the flow of pulsed oxygen in response to the breathing detector sensor 112 detecting the user breathing through the oxygen mask 110 and dispense a pressure and time regulated flow of the oxygen prescription delivery amount of the pulsed oxygen to the oxygen mask 110 for a duration of the pulse delivery time (task 1112).

Process 1100 may continue by providing a portable electronic power module such as the portable electronic power module 116 operable to power a portable pulse oxygen system such as the portable pulse oxygen system 100 (task 1114).

Process 1100 may continue by packaging the portable pulse oxygen system 100 in a package such as the package 200 substantially similar in size to a chemical oxygen system and operable to be used as a direct replacement for the chemical oxygen system (task 1116).

Process 1100 may continue by installing the package 200 in an enclosed volume (task 1118). The enclosed volume may comprise, for example but without limitation, an aircraft cabin, a train cabin, a bus cabin, a spacecraft cabin, a vehicle cabin, a submarine cabin, an interior of a building, or other enclosed volume.

In this way, various embodiments of the disclosure provide a low complexity, low weight, optimally secure system and methods for providing pulsed oxygen to a user.

While at least one example embodiment has been presented in the foregoing detailed description, it should be appreciated that a vast number of variations exist. It should also be appreciated that the example embodiment or embodiments described herein are not intended to limit the scope, applicability, or configuration of the subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The above description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. Thus, although FIGS. 1-9 depict example arrangements of elements, additional intervening elements, devices, features, or components may be present in an embodiment of the disclosure.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future.

Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The term "about" when referring to a numerical value or range is intended to encompass values resulting from experimental error that can occur when taking measurements.

As used herein, unless expressly stated otherwise, "operable" means able to be used, fit or ready for use or service, usable for a specific purpose, and capable of performing a recited or desired function described herein. In relation to systems and devices, the term "operable" means the system and/or the device is fully functional and calibrated, comprises elements for, and meets applicable operability requirements to perform a recited function when activated.

The invention claimed is:

1. A method for providing pulsed supplemental oxygen to a user, comprising:
providing to a user an oxygen mask coupled through a mask hose to a metering valve, the metering valve configured in a packaged pulsed oxygen system comprising a canister containing the metering valve, an oxygen container, a breathing detector sensor directly coupled to the metering valve, and a controller, the pulsed oxygen system operable to be used as a direct replacement for a chemical oxygen system;
determining an oxygen prescription delivery amount based on and as a function of a real-time operation condition;
calculating a metering valve timing based on the oxygen prescription delivery amount to obtain a pulse delivery time; and
dispensing a pressure and time regulated flow of the oxygen prescription delivery amount of pulsed oxygen to the oxygen mask for a duration of the pulse delivery time in response to detecting the user breathing through the oxygen mask.

2. The method of claim 1, wherein the step of determining further comprises accessing the oxygen prescription delivery amount.

3. The method of claim 1, wherein the real-time operation condition comprises pressure in a decompressed aircraft cabin.

4. The method of claim 1, wherein the user is onboard a decompressed aircraft cabin.

5. A packaged pulsed oxygen system, comprising:
a breathing detector sensor;
a metering valve timing calculation module operable to calculate a metering valve timing to provide a pulse delivery time based on an oxygen prescription delivery amount corresponding to a real-time operation condition;
a metering valve directly coupled to the breathing detector sensor and operable to:
provide a flow of pulsed oxygen in response to detecting a user breathing through an oxygen mask; and
dispense a pressure and time regulated flow of the oxygen prescription delivery amount of the flow of the pulsed oxygen through a mask hose to the oxygen mask for a duration of the pulse delivery time;

an oxygen container; and a canister containing the metering valve, the breathing detector sensor, the oxygen container, and the metering valve timing calculation module, and configured to provide the packaged pulsed oxygen system operable to be used as a direct replacement for a chemical oxygen system.

6. The system of claim 5, wherein the breathing detector sensor is operable to initiate the flow of the pulsed oxygen in response to detecting the user breathing through the oxygen mask.

7. The system of claim 5, further comprising an operation condition sensor contained within the canister and operable to detect the real-time operation condition.

8. The system of claim 5, wherein the real-time operation condition comprises at least one member selected from the group consisting of: a pressure in a decompressed aircraft cabin, a pressure in a decompressed high speed train, a pressure in high altitudes mountains, a pressure in a high smoke environments, and a temperature.

9. The system of claim 5, further comprising a portable electronic power module contained within the canister and operable to power the pulse oxygen system.

10. The system of claim 5, further comprising an oxygen prescription delivery amount database operable to provide the oxygen prescription delivery amount based on and as a function of a real-time operation condition.

11. The system of claim 5, further comprising the oxygen mask operable to provide the flow of the pulsed oxygen to the user.

12. A method for providing a portable pulsed oxygen system in a portable pulsed oxygen package, comprising:

providing a breathing detector sensor;

providing a metering valve timing calculation module operable to calculate a metering valve timing based on an oxygen prescription delivery amount to obtain a pulse delivery time;

providing a metering valve directly coupled to the breathing detector sensor and operable to:

provide a flow of pulsed oxygen in response to detecting a user breathing through an oxygen mask; and dispense a pressure and time regulated flow of the oxygen prescription delivery amount of the flow of the pulsed oxygen through a mask hose to the oxygen mask for a duration of the pulse delivery time;

providing an oxygen container; and configuring a canister to contain the metering valve, the breathing detector sensor, the oxygen container, and the metering valve timing calculation module, and to provide the portable pulsed oxygen system operable to be used as a direct replacement for a chemical oxygen system.

13. The method of claim 12, wherein the breathing detector sensor is operable to initiate the flow of the pulsed oxygen in response to detecting the user breathing through the oxygen mask.

14. The method of claim 12, further comprising providing an operation condition sensor coupled to a controller and operable to detect a real-time operation condition, wherein the controller is contained in the canister and comprises the metering valve timing calculation module, and the pulse delivery time is based on the real-time operation condition.

15. The method of claim 14, wherein the real-time operation condition comprises at least one member selected from the group consisting of: a pressure in a decompressed aircraft cabin, a pressure in a decompressed high speed train, a pressure in high altitudes mountains, a pressure in a high smoke environments, and a temperature.

16. The method of claim 12, further comprising providing an oxygen prescription delivery amount database.

17. The method of claim 12, further comprising providing a portable electronic power module contained in the canister and operable to power the portable pulse oxygen system.

18. The method of claim 12, further comprising installing the packaged pulsed oxygen system in an enclosed volume.

19. The method of claim 18, wherein the enclosed volume is an aircraft cabin.

20. The method of claim 12, further comprising providing the oxygen mask operable to provide the flow of the pulsed oxygen to the user.

* * * * *